US010693119B2

(12) United States Patent
Wyser et al.

(10) Patent No.: US 10,693,119 B2
(45) Date of Patent: Jun. 23, 2020

(54) ACCUMULATOR AND METHOD FOR THE MANUFACTURE THEREOF

(71) Applicant: WYON AG, Appenzell Steinegg (CH)

(72) Inventors: Paul Wyser, Appenzell-Steinegg (CH); Remo Sutter, Lustmuehle (CH)

(73) Assignee: WYON AG, Appenzell Steinegg (CH)

( * ) Notice: Subject to any disclaimer, the term of this patent is extended or adjusted under 35 U.S.C. 154(b) by 0 days.

(21) Appl. No.: 16/042,734

(22) Filed: Jul. 23, 2018

(65) Prior Publication Data

US 2019/0081313 A1  Mar. 14, 2019

(30) Foreign Application Priority Data

Sep. 13, 2017 (EP) .................................. 17190870

(51) Int. Cl.
| | | |
|---|---|---|
| H01M 2/30 | (2006.01) | |
| H01M 2/26 | (2006.01) | |
| H01M 10/04 | (2006.01) | |
| H01M 2/02 | (2006.01) | |
| A61N 1/378 | (2006.01) | |
| A61M 5/142 | (2006.01) | |
| H04R 25/00 | (2006.01) | |
| A61N 1/36 | (2006.01) | |

(52) U.S. Cl.
CPC ............ *H01M 2/266* (2013.01); *A61N 1/378* (2013.01); *H01M 2/0207* (2013.01); *H01M 2/26* (2013.01); *H01M 10/049* (2013.01); *A61M 5/14276* (2013.01); *A61M 2205/8206* (2013.01); *A61N 1/36036* (2017.08); *H04R 25/602* (2013.01); *H04R 2225/31* (2013.01)

(58) Field of Classification Search
CPC ...... H01M 2/266; H01M 2/26; H01M 2/0207; H01M 10/049; H01M 10/0427; H01M 2/0222; A61N 1/378; A61N 1/36036; A61M 2205/8206; A61M 5/14276; H04R 25/602; H04R 2225/31
See application file for complete search history.

(56) References Cited

U.S. PATENT DOCUMENTS

| | | |
|---|---|---|
| 7,294,430 B2 | 11/2007 | Wyser |
| 8,685,560 B2 | 4/2014 | Wyser |
| 2003/0171784 A1 | 9/2003 | Dodd et al. |
| 2012/0100406 A1 | 4/2012 | Gaugler |
| 2014/0072860 A1 | 3/2014 | Inauen |

FOREIGN PATENT DOCUMENTS

| | | |
|---|---|---|
| DE | 10 2009 060 800 A1 | 6/2011 |
| EP | 1 100 138 A1 | 5/2001 |
| EP | 1 530 247 A2 | 5/2005 |
| WO | WO 2012/057854 A1 | 5/2012 |

*Primary Examiner* — Cynthia K Walls
(74) *Attorney, Agent, or Firm* — Birch, Stewart, Kolasch & Birch, LLP

(57) ABSTRACT

An accumulator, specifically a small accumulator, comprises at least two positive electrodes, each with a contact terminal, and at least two negative electrodes, each with a contact terminal. The accumulator further comprises at least one contacting device having at least one contacting element which is arranged between two adjoining contact terminals and interconnects said two adjoining contact terminals in an electrically conductive manner. The accumulator further comprises a housing, which entirely accommodates the at least two positive electrodes, the at least two negative electrodes and the at least one contacting device. The accumulator comprises at least one cladding structure, which encloses the at least one contacting device.

12 Claims, 9 Drawing Sheets

ACCUMULATOR AND METHOD FOR THE MANUFACTURE THEREOF

TECHNICAL FIELD

The invention relates to an accumulator, specifically a small accumulator for the storage and release of electrical energy. The invention further relates to the application of an accumulator according to the invention in a medical device, specifically in a medical device which is implantable in the human body. The invention further relates to a method for the manufacture of the accumulator according to the invention.

BACKGROUND ART

Accumulators are employed as a network-independent electric power supply in a variety of portable and stationary devices. In devices with a high energy demand, including, for example, hearing aids, drug dispensers and/or diagnostic devices, primary cells can also be employed, although these have the disadvantage that, conversely to accumulators, these are not rechargeable, and must be replaced every five to ten days.

From DE 10 2009 060 800 A1 (VARTA, 2011), button cells with wound electrodes and cup-shaped metal housings for accumulators and non-rechargeable batteries are known. In practice, button cells of this type are employed for structural heights in excess of 5 mm. For smaller structural heights, the wound design is disadvantageous, on the grounds of the excessively small active volume. Button cells with a metal housing are, moreover, restricted in their shape. In turn, this prevents the optimum exploitation of an available volume in a device which is to be operated by a button cell and, in consequence, reduces the capacity of the button cell.

US 20140072860 A1 (SWISSBAT, 2014) discloses an accumulator with a plastic housing and a stacked electrode design. The conductor tabs of the anode and cathode are respectively positioned on a metal block and welded together. The relatively large space requirement for the conductor block and the conductor tabs is disadvantageous. Consequently, this design is largely unsuitable for accumulators of a small size or the smallest size such as, for example, button cells. Moreover, automatic stacking of the electrodes, on the grounds of the different lengths and different angles of the conductor tabs, is a very difficult and expensive process.

From EP 1 100 138 A (Wyon A G, 2001), an accumulator is known of a space-saving and customized design, having wound electrodes, integrated protective and charging circuitry and a plastic housing, in order to permit the replacement of conventional zinc-air primary cells in fields of application with a high energy demand including, for example, auditory implants. The current terminal is of tubular design, the abutment of which against the housing base is associated with a loss of space. Moreover, electrical contacting by means of pins which project into the housing is not suitable for devices, the batteries of which require frequent replacement.

U.S. Pat. No. 7,294,430 B2 (Wyon A G, 2007) therefore proposes a mechanically-tensionable connection and a contact terminal on the outer side of the housing, in the interests of straightforward contacting with a device. However, this form of construction is unsuitable for accumulators with wound electrodes and a structural height of less than 6 mm, on the grounds of the relatively small active volume.

In order to achieve a space-saving arrangement of electrodes in button cells, with a simultaneously high efficiency, U.S. Pat. No. 8,685,560 (Wyon, 2014) proposes folded electrodes in a metal housing.

SUMMARY OF THE INVENTION

The object of the invention is to create an accumulator pertaining to the above-mentioned technical field, having an exceptionally high capacity and/or energy density. Specifically, the object of the invention is the maximization of the space available for the active material in an accumulator of predefined external dimensions. A further object of the invention is the creation of an efficient and cost-effective production method for an accumulator according to the invention. Moreover, a particularly effective application for an accumulator according to the invention shall be provided.

The solution of this object is defined by the features of claim 1. According to the invention, an accumulator, specifically a small accumulator, for the storage and release of electrical energy comprises at least two positive electrodes, each with a contact terminal, and at least two negative electrodes, each with a contact terminal. The accumulator further comprises at least one contacting device having at least one contacting element, which is arranged between two adjoining contact terminals and interconnects said two adjoining contact terminals in an electrically conductive manner. The accumulator further comprises a housing, which entirely accommodates the at least two positive electrodes, the at least two negative electrodes, and the at least one contacting device. The accumulator comprises at least one cladding structure, which encloses the at least one contacting device.

The cladding of the at least one contacting device permits a highly space-saving design thereof, as the customary and spatially cumbersome angulation and direct welding of all the contact terminals of the electrodes can be omitted. The cladding functions as a guide and/or retainer for the contacting elements, which can therefore be of very compact design and occupy a far smaller space than that required for the customary angulation and direct welding of all the contact terminals. Accordingly, more space is available in the interior of the accumulator housing for the active electrode material, also described as the active material. Consequently, the accumulator can have a higher capacity and/or energy density than an accumulator having no such cladding of the at least one contacting device. Moreover, the cladding of the at least one contacting device can provide protection against unwanted deposits. The cladding can, for example, protect a contacting device which is connected to the negative electrodes against lithium deposits. A contacting device with cladding can be produced for an accumulator of structural height as small as 1 mm or greater. Tests have shown that, in an accumulator according to the invention, the energy content can be increased by 10%-20%, in relation to a conventional accumulator.

An accumulator is to be understood as a rechargeable storage for electrical energy, operating on an electrochemical basis. A single rechargeable storage element is described as a secondary element or a secondary cell. Conversely, a primary cell is not rechargeable, or is only rechargeable to a very limited extent. An accumulator can comprise one, or a plurality of secondary cells. If the accumulator comprises a plurality of secondary cells, these can be electrically interconnected, either in series, in order to increase the useful electrical voltage, or in parallel, in order to increase the useful capacity.

Small accumulators are accumulators with a volume of less than 30 cm$^3$, specifically with a volume of less than 10 cm$^3$, and more specifically with a volume of less than 1 cm$^3$. Small accumulators may be button cells. Button cells may have a round shape, wherein their diameter is greater than their height. However, small accumulators can also be of cuboid design, or can assume any other device-specific shape including, for example, a horseshoe shape or a teardrop shape. A device-specific shape is to be understood as a shape which corresponds to the available space for an accumulator in the device, into which the accumulator is to be inserted. Small accumulators can assume a structural height of 6 mm or less, specifically of 5 mm or less. Small accumulators preferably comprise a single secondary cell which, in turn, can comprise a plurality of parallel-connected electrodes. Small accumulators can have a rated voltage in the range of 1 V to 5 V, specifically of 1.3 V to 4 V, and more specifically of 3 V to 3.8 V.

The electrodes can be of a layered design. Each electrode comprises an active material. An anode material is applied to the negative electrode, and a cathode material is applied to the positive electrode. The electrodes can be coated on one side or on both sides with active material. The electrodes can be configured in a stacked arrangement. In a corresponding stack, a positive electrode follows a negative electrode in sequence. A separator is arranged in between, as a separating layer. A stack of electrodes can comprise a plurality of electrodes.

The contact terminal of an electrode can be a conductive grid, a conductive carrier band and/or a conductive foil, such as, for example, a tab. The contact terminal is connected to a positive electrode or to a negative electrode in an electrically conductive manner, and is free of active material. The contact terminal of a positive or a negative electrode can be straight or angled. An angled contact terminal can be longer than a straight contact terminal, but otherwise assumes the same shape.

The contacting device forms an electrically-conductive connection between the contact terminals of the electrodes. Preferably, the contacting device forms a conductive connection between electrodes having the same active material. A contacting device can thus specifically interconnect the contact terminals of positive electrodes, such that the positive electrodes are electrically connected in parallel, or can specifically interconnect the contact terminals of negative electrodes, such that the latter are electrically connected in parallel. The contacting device can be of a column-type design and/or of a cascade-type design. Preferably, the contact device has a round, oval or angular cross-section, for example a rectangular cross-section.

The at least one contacting element can be entirely or partially formed of an electrically conductive material. Preferably, the at least one contacting element, for use in combination with positive electrodes, comprises a metal such as, for example, aluminum, non-corroding nickel steel or titanium. For the application of the at least one contacting element in combination with negative electrodes, the contacting element preferably comprises a metal such as, for example, copper, non-corroding nickel steel or titanium. Alternatively and/or additionally, the at least one contacting element can also be entirely or partially coated with a conductive material. The at least one contacting element can be electrolyte-resistant and/or corrosion resistant. The contacting element can assume a round, oval or angular cross-section, for example a rectangular cross-section.

The height of a contacting element preferably corresponds to the clearance between two directly adjoining contact terminals, or to a whole-number multiple thereof. For example, two respectively directly adjoining contact terminals can be mutually angled and interconnected with no clearance, i.e. without the interposition of a contacting element. The newly-resulting adjoining contact terminals will thus have double the clearance of directly adjoining, but non-angled contact terminals. Consequently, the at least one contacting element will then also assume double the height. Correspondingly, three or more directly adjoining contact terminals can be combined, such that the height of the contacting element then corresponds to three times, or a higher multiple of the clearance between two directly adjoining contact terminals.

The housing preferably comprises a housing bushing, in order to allow for an electrically-conductive connection between the at least one contacting device and an external contact of the accumulator. The at least one contacting device can thus extend into the housing bushing. A housing which entirely accommodates the at least one contacting device has the advantage that, apart from the above-mentioned housing bushing, no further housing bushing is required for the accommodation of the at least one contacting device, and potential losses of leak-tightness in the housing can be minimized.

The housing can be gas-tight, electrolyte-resistant, corrosion-resistant and/or electrically-insulating. Gas-tight housings permit a long service life of the accumulator, as no outgassing of the accumulator is possible, and no unwanted substances can diffuse into the interior of the housing. Advantageously, the housing can be comprised of two parts, which are interconnected in a gas-tight manner during the manufacture of the accumulator according to the invention. For example, the housing can consist of a housing receptacle and a housing cover.

According to the invention, by the term gas-tight, it is to be understood that gas diffusion, specifically water vapor diffusion, does not occur, or is negligible. By the term insulating, it is to be understood that a conductivity of less than $10^{-6}$ S/m is present. Specifically, the term insulating corresponds to the conductivity of a non-conductor, or of a material or combination of materials which is known as an insulator.

An external contact of the accumulator can be the negative pole or the positive pole of the accumulator. The negative pole and the positive pole of the accumulator can be located on an outer side of the housing, and can be easily accessible. The external contacts can be configured to as small and as flat a design as possible, and are preferably located on an edge of the housing. An external contact can be formed of non-corroding gilded steel, gilded brass, copper, titanium or gold. Wires can be soldered or welded to the external contacts, or the external contacts can be mounted directly on a circuit board.

The cladding can enclose half or more than half the perimeter of the at least one contacting device, and particularly can enclose two-thirds of more of the perimeter of the at least one contacting device. In each case, the cladding leaves a proportion of the perimeter of the contacting device exposed, for example, the cladding can leave one fifth or more than one fifth of the perimeter of the contacting device exposed. The perimeter of the contacting device can be determined along the external outer edge of the cross-section thereof, as indicated above.

The cladding can tightly enclose the contacting device to the extent that the flow path of ions through the electrolyte to the contacting device is prolonged, such that practically no ions reach the contacting device through the electrolyte, and any corresponding material depositions on the contacting device, such as lithium depositions, are prevented accordingly.

The wall thickness of the cladding can lie within a range of 0.005 mm to 1 mm, in particular within a range of 0.01 mm to 0.6 mm, and more particularly within a range of 0.15 mm to 0.4 mm.

In a preferred embodiment, the contacting device comprises a clamping device, which clamps the at least one contacting element to the at least two adjoining contact terminals.

By this arrangement, it is achieved that the electrical transfer resistance and/or electrical contact resistance between the at least one contacting element and the at least two adjoining contact terminals is minimized to the greatest possible extent. This reduces the internal resistance of the accumulator and improves the efficiency thereof.

Alternatively and/or additionally to the clamping device, a conductive rod or wire can be welded or soldered to the at least one contacting element and the two adjoining contact terminals. Bonded connections or adhesive bonds by means of a conductive adhesive are also possible.

In a further preferred embodiment, the at least two adjoining contact terminals each comprise a hole. The at least one contacting element is a sleeve. The clamping device comprises a pin and a counter-bearing. The pin, in a region of a first end, has a flange and, in a region of a second end, has a connection to the counter-bearing. The pin is routed through the holes in the at least two adjoining contact terminals and through the at least one contacting element. The at least two adjoining contact terminals and the at least one contacting element are arranged between the flange and the counter-bearing.

The clamping device and the contacting device can thus be manufactured in a particularly simple manner. The pin can, moreover, be employed to form a simple and reliable electrical connection with an external contact of the accumulator.

The at least one contacting element, specifically the at least one sleeve, can be formed, for example, of a metal such as copper, aluminum, gold, silver or titanium. These metals have good conductivity and are corrosion-resistant. The at least one contacting element, specifically the at least one sleeve, can also be comprised of metal compounds. The at least one sleeve can have an internal diameter between 0.1 mm and 2 mm, specifically between 0.2 mm and 1 mm, more specifically between 0.4 mm and 0.8 mm, and especially between 0.3 mm and 0.6 mm. The external diameter of the at least one sleeve is then between 0.2 mm and 4 mm, or specifically between 0.4 mm and 2 mm, or more specifically between 0.6 mm and 1.5 mm.

Alternatively, the at least one contacting element and/or the at least one sleeve can also consist of one or more non-metallic materials including, for example, a conductive plastic. The at least one contacting element can also contain, for example, one or more organic materials including, for example, carbon, specifically structural carbon.

Advantageously, the pin can entirely or partially consist of a conductive material. Preferably, the pin, for use in combination with positive electrodes, consists of a metal such as, for example, aluminum, non-corroding nickel steel or titanium. For use in combination with negative electrodes, the pin preferably consists of a metal such as, for example, copper, non-corroding nickel steel or titanium. Alternatively and/or additionally, the pin can also be entirely or partially coated with a conductive material. Alternatively, the pin can also consist of one or more non-metallic materials including, for example, a conductive plastic. The pin can also contain, for example, one or more organic materials including, for example, carbon, specifically structural carbon.

Preferably, the pin has a round, oval or angular cross-section, and can, for example, assume a rectangular cross-section. If the pin has a round cross-section, it can have an external diameter between 0.1 mm and 2 mm, specifically between 0.2 mm and 1 mm, and more specifically between 0.4 mm and 0.8 mm. For other cross-sectional shapes, the pin can assume cross-sectional areas between 0.01 $mm^2$ and 3 $mm^2$, specifically between 0.03 $mm^2$ and 1 $mm^2$, and more specifically between 0.1 $mm^2$ and 0.3 $mm^2$. Advantageously, the pin has external dimensions which essentially correspond to the internal dimensions of the at least one sleeve, or are slightly smaller than the internal dimensions of the at least one sleeve, thus permitting an easy push-fit of the at least one sleeve onto the pin. Preferably, the external diameter or the external dimensions of the pin are constant along the length thereof—with the exception of the flange. Alternatively, the external diameter of the pin can also vary along the length thereof.

Alternatively, the external dimensions of the pin can also be slightly greater than the internal dimension of the at least one sleeve. The at least one sleeve can then be mounted on the pin by press-fitting.

The counter-bearing can be a contacting element, specifically a sleeve. For example, a press-fitted sleeve can constitute a counter-bearing.

Alternatively to the pin, a tube with a longitudinal slot can also be employed. In place of sleeves, spacers with no through-hole can then be employed. Through the longitudinal slot in the tube, the contact terminals of the electrodes can be inserted in the tube. Between two adjoining contact terminals, a spacer can be arranged in the tube. At one end of the tube, the internal diameter of the tube comprises a taper, thus constituting a support for the contact terminals and the spacers, analogously to the flange in the preferred embodiment of the clamping device, incorporating a pin.

Alternatively and/or additionally to the at least one sleeve, a comb can be employed. Between the teeth of the comb, the contact terminals of the electrodes can be accommodated, such that the comb and the contact terminals are interconnected in an electrically conductive manner, for example in the form of a clamped or crimped connection. The comb has the advantage, that neither a pin nor a tube are required. For production purposes, however, the preferred embodiment with at least one sleeve has advantages.

In a further preferred embodiment, the connection of the pin to the counter-bearing is a threaded connection, a riveted connection and/or a welded connection.

Connections of this type are very easily produced, and are highly reliable. For example, a contacting element which is arranged on an end of the pin which is averted from the flange-bearing end can be screwed onto the pin. Alternatively, a contacting element of this type can also be riveted or welded to the pin.

Alternatively and/or additionally, the connection of the pin to the counter-bearing can also be realized by soldering, gluing and/or interference fitting including, for example, press-fitting. In the last of these cases, the counter-bearing is press-fitted to the pin.

In a further preferred embodiment, the contact terminals of the at least two positive electrodes are adjoining and/or the contact terminals of the at least two negative terminals are adjoining.

Accordingly, an electric parallel connection of the at least two positive electrodes and/or a parallel connection of the at least two negative electrodes can be formed. A parallel connection of electrodes permits an increase in the capacity and/or in the energy density of the accumulator.

Alternatively to a parallel connection of electrodes, the contact terminals can be arranged such that a contact terminal of a positive electrode of the at least two positive electrodes, and a contact terminal of a negative electrode of the at least two negative electrodes, are adjoining. In this case, a series connection of electrodes is implementable, when the latter are associated with different secondary cells. Insulators can also be employed, where no conductive connection between two adjoining contact terminals is required for the formation of a series circuit, which conductive connection would result in a short-circuit.

In a further preferred embodiment, the accumulator comprises two contacting devices, both of which are entirely arranged within the housing.

Thus, in comparison with embodiments having only one contacting device, a design with superior space saving is achieved. As both contacting devices are entirely arranged within the housing, the number of housing bushings can be minimized, and any potential losses of leak-tightness in the housing can also be minimized accordingly.

Each of the two contacting devices can comprise a cladding.

In a further preferred embodiment, the cladding is consisting of a plastic.

A plastic cladding can be easily manufactured, for example by injection-molding. A plastic cladding can be electrolyte-resistant, corrosion-resistant and/or electrically insulating. If the accumulator comprises two contacting devices, both claddings can be consisting of plastic and integrally formed, for example as a spectacle-shaped plastic molding. A plastic cladding or two plastic claddings can be employed, for example, in a housing of metal construction.

Advantageously, plastics such as liquid crystal polymers (LCP) or polyethylene (PE) can be employed for the cladding. The cladding can also contain reinforced LCP.

Where a metal housing is used, at least one contacting device, specifically where two contacting devices are employed in the accumulator, can be configured in an electrically insulated arrangement from the housing, which can be achieved by means of at least one plastic cladding.

Alternatively, the cladding can also be of metal construction. If the housing is comprised of two parts, respectively of metal construction, the cladding can be integrated in one part of said two parts of the housing. Where two claddings are provided, one cladding can be integrated in each part of the two parts of the housing.

In a further preferred embodiment, the housing is consisting of a plastic.

Such housings can be manufactured in a simple and cost-effective manner, and to customized dimensions, for example by means of injection-molding. A housing of plastic construction can be electrolyte-resistant, corrosion-resistant and/or electrically insulating. In an electrically insulating housing, there is no requirement for the maintenance of a safety clearance between the inner wall of the housing and the active material, but rather the active material can lie in contact with the housing, such that more active material can be accommodated in the accumulator than in an accumulator with an electrically conductive housing. Likewise, by an accurate adaptation of the accumulator in a device which, in the case of a plastic housing, is particularly simple to achieve, an even higher energy content can be obtained. In a plastic housing, there is virtually no restriction with respect to shaping.

Advantageously, a LCP plastic (liquid crystal polymer) is employed for the housing. The housing can also contain reinforced LCP.

The plastic housing can have a wall thickness of less than 0.5 mm, specifically of less than 0.3 mm, and more specifically of 0.2 mm, or less. In small accumulators, wall thickness assumes a key role in that, in an accumulator of given external dimensions, a reduction in wall thickness can be employed as a means of introducing more active material into the housing, thereby increasing the capacity of the accumulator.

If not only the housing, but also the cladding or the two claddings are comprised of metal, the cladding or the two claddings can be integrated in one part of the housing, for example in a housing receptacle. In this case, the housing receptacle and the one cladding can be manufactured integrally and/or the housing receptacle and the two claddings can be manufactured integrally, thereby simplifying the production and/or assembly of the accumulator. Moreover, integration of the cladding or the claddings in the housing constitutes a further space saving, which can be employed as a means of increasing the active material, and thus the capacity of the accumulator.

Alternatively, the housing can also be of metal construction. By this arrangement, the accumulator is highly robust vis-à-vis external mechanical influences.

In a further preferred embodiment, the housing comprises an eye which is arranged on an outer side of the housing.

The eye can be employed for the fastening of the accumulator to a device, or the eye can be employed for the fastening of an object to the accumulator.

The eye can be arranged on an outer side of a housing base, on an outer side of a housing cover, or on an outer side of a housing sidewall. A plurality of eyes can also be fitted to one or more outer sides of the housing, for example to an outer side of a housing base, to an outer side of a housing cover and/or to an outer side of a housing sidewall.

Alternatively, the accumulator can also be configured with no eye, or with another means of fastening.

In a further preferred embodiment, at least one of the negative electrodes comprises a current conductor of an electrically conducting non-metallic structural material.

A current conductor of an electrically conductive non-metallic structural material has the advantage that it is corrosion-resistant and can, moreover, be more cost-effective than, for example, a corrosion-resistant metal. Corrosion-resistant current conductors improve the service life of the accumulator. Moreover, by the application of a current conductor of an electrically conductive non-metallic structural material, it is not necessary to fit metallic contacting elements such as, for example, metal terminal tabs to the electrodes. The current conductor of an electrically conductive non-metallic structural material can be employed, in a region where, for example, no active material is present, as a contact terminal. This non-metallic contact terminal and/or plurality of non-metallic contact terminals can be brought directly into contact with one or more contacting elements, thereby constituting a contacting device.

The electrically conductive non-metallic structural material can consist of an electrically conductive plastic and/or an electrically conductive organic material or material mixture such as, for example, structural carbon. Structural carbon is distinguished from the carbon which is employed as an active material.

Preferably, the current conductor can be configured of structural carbon in the form of a film or a sheet material.

A film and/or sheet of structural carbon can constitute a carrier band for the accommodation of the active material.

Preferably, at least one positive electrode can also comprise a current conductor of structural carbon construction.

For further details of current conductors formed of an electrically conductive non-metallic structural material, reference is made to the European Patent application entitled "Rechargeable Battery", filed by the same applicant on the same date of application as the present patent application.

Preferably, the accumulator can be a rechargeable lithium or lithium-ion battery.

A further aspect of the invention relates to the use of an accumulator according to the invention. The accumulator according to the invention is used in a medical device, specifically in a hearing aid, and more specifically in a medical device which is implantable in the human body.

As a result of the increased capacity of the accumulator according to the invention, the time interval between charging operations can be extended, to the greater convenience of the user of the device.

Medical devices can include, for example, diagnostic devices, hearing aids and/or implantable devices such as, for example, implantable pumps or auditory implants.

A further aspect of the invention relates to a method for manufacturing an accumulator according to the invention. The method comprises the following steps:

a) the alternating insertion of a positive electrode with a contact terminal and a negative electrode with a contact terminal in a housing, such that the contact terminal of the positive electrode is arranged in a cladding and/or such that the contact terminal of the negative electrode is arranged in a cladding,
b) the application of a contacting element to the contact terminal of a positive electrode and/or the application of a contacting element to the contact terminal of a negative electrode,
c) repetition of step b),
d) production of at least one contacting device by the formation of an electrically conductive connection between the contacting element and two adjoining contact terminals.

A manufacturing method of this type is highly effective, and can be substantially automated. This results in a high and reproducible quality of accumulators, with attractive production costs. Moreover, a manufacturing method of this type is also highly suitable for small accumulators.

If both the contact terminals of the positive electrodes are accommodated in a cladding, and the contact terminals of the negative electrodes are accommodated in a cladding, this does not necessarily involve one and the same cladding, but can involve two spatially separate claddings.

In a preferred embodiment, step d) of the method for manufacturing an accumulator according to the invention includes riveting, screwing and/or welding of a counter-bearing to a pin.

In this way, the contacting device can be manufactured in an exceptionally simple manner, with high quality and with good electrical properties, specifically with low transfer resistances.

In a further preferred embodiment, the method for manufacturing an accumulator according to the invention additionally comprises one or more of the following steps:

e) the punch-out and ablation of the positive electrodes and the negative electrodes according to predefined shapes, and/or
f) the at least partial coating of a pin with a seal, and/or
g) press-fitting of a pin through a housing bushing in the receptacle base to an external contact, and/or
h) welding of the negative electrodes in one separator respectively, and/or
i) drying, insertion of electrolyte, gas-tight fitting of the housing cover and formation of the accumulator.

The punch-out and ablation of electrodes ensures an optimum fit of electrodes in the interior of the housing, and thus an optimum capacity of the accumulator.

The at least partial coating of a pin with a seal permits a gas-tight penetration of the pin through a housing bushing in the receptacle base. The seal can also be configured as an adhesive or an O-ring.

The press-fitting of a pin through a housing bushing in the receptacle base to an external contact permits the simple formation of the connection between an external contact of the accumulator and the contacting device. Moreover, a highly space-saving external contact can be formed accordingly which, moreover, can be mounted directly on a circuit board.

The welding of the negative electrodes in one separator respectively ensures a reliable long-term operation of the accumulator.

Drying, the insertion of electrolyte, the gas-tight fitting of the housing cover and the formation of the accumulator also ensure a reliable long-term operation of the accumulator.

By means of the present invention, it is possible to provide accumulators with high energy density, even with small structural designs, and having a high degree of security against internal short-circuits and dendrite formation, whereby said accumulators primarily can be particularly advantageously employed in medical devices.

Further advantageous embodiments and combinations of features of the invention result from the following detailed description, and from the patent claims in their entirety.

BRIEF DESCRIPTION OF THE DRAWINGS

In the drawings employed for the illustration of the exemplary embodiment.

In the figures, in principle, identical components are identified by the same reference symbols.

PREFERRED EMBODIMENTS

Figure 1:
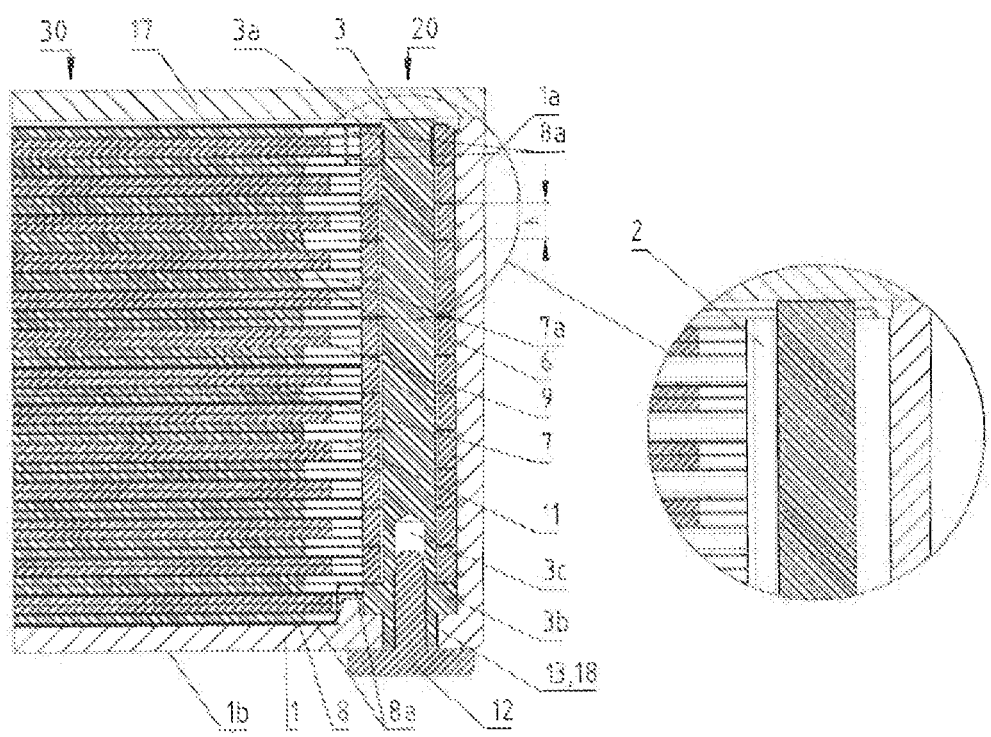
FIG. 1 shows a cross-section of a first exemplary embodiment, with a screw-fitted sleeve.

FIG. 1 shows a cross-section of a first exemplary embodiment of the accumulator according to the invention, in the region of a contacting device 20 for positive electrodes. In a housing receptacle 1, consisting of a receptacle wall 1a and a receptacle base 1b, below the housing cover 17, a stack 30 is located, comprising of positive electrodes 7 which are coated on both sides with active material, and negative electrodes 9 which are coated on both sides with active material. The positive straight contact terminals 7a of the positive electrodes 7 which are coated on both sides lead to the contacting device 20. The stack 30 further comprises a plurality of separators 11. One separator 11 respectively is arranged between a positive electrode 7 and a negative electrode 9. At the very bottom of the stack 30, directly on the receptacle base 1b a positive electrode 8 is arranged which is coated on one side with active material. The positive angled contact terminal 8a thereof leads to the contacting device 20.

The contacting device 20 comprises a pin 3 and a plurality of contacting elements 6. The pin 3, in the region of a first lower end, comprises a flange 3b. The flange 3b bears on the receptacle base 1b. The first lower end of the pin 3 is arranged in a housing bushing 13, which is located in the receptacle base 1b. A seal 18 forms a gas-tight connection between the pin 3 and the receptacle base 1b. In the region of the first, lower end of the pin 3, the pin 3 further comprises a bore 3c, into which an external contact 12 is press-fitted, which projects beyond part of the underside of the receptacle base 1b. The receptacle base 1b, in the region of the housing bushing 13, is thus clamped between the external contact 12 and the flange 3b, thus contributing to the formation of a gas-tight seal in the housing bushing 13. For this reason, the first, lower end of the pin 3 does not extend entirely into the housing bushing 13, but a small clearance is provided between the end face of the first, lower end of the pin 3 and the external contact 12. Correspondingly, the external contact 12 does not extend entirely into the bore 3c, but here again a degree of clearance is provided. Additionally, in the region in which the housing is clamped between the external contact 12 and the flange 3b of the pin 3, an (not shown) sealing material can also be located. The external contact 12 is electrically connectable to the (not shown) device in which the accumulator according to the invention is installed. In FIG. 1, the external contact 12 constitutes the positive pole of the accumulator. The contacting device 20 is then built up as follows: on the flange 3b of the pin 3, the positive angled contact terminal 8a is arranged. This is followed by a positive straight contact terminal 7a. This is followed by an alternating arrangement of a contacting element 6 in the form of a sleeve and a positive straight contact terminal 7a. At the uppermost end of the stack 30, directly below the housing cover 17, a positive electrode 8 which is coated on one side with active material is arranged. The positive angled contact terminal 8a thereof also leads to the contacting device 20, and is arranged on a positive straight contact terminal 7a. Above this a final contacting element 6 is located which, in the present first exemplary embodiment, is provided with a screw thread 3a, and onto which a pin 3 provided with a corresponding screw thread 3a is screwed. Accordingly, all the positive contact terminals 7a, 8a and the contacting elements 6 are clamped between the flange 3b and the uppermost screwed on contacting element 6, which functions as a counter-bearing, such that there is the lowest possible contact resistance between the positive contact terminals 7a, 8a, the contacting elements 6 and the pin 3. As the external contact 12 is compressed against the pin 3, here again a minimal contact resistance is provided. The height h of a contacting element 6 is dimensioned such that it corresponds to the clearance between two directly adjoining positive straight contact terminals 7a. In the present first exemplary embodiment, the height h of the contacting element 6 corresponds to the thickness of a positive electrode 7 which is coated on both sides, plus the thickness of a negative electrode 9 which is coated on both sides, plus the thickness of two separators 11, and minus the thickness of a positive straight contact terminal 7a.

Figure 2:
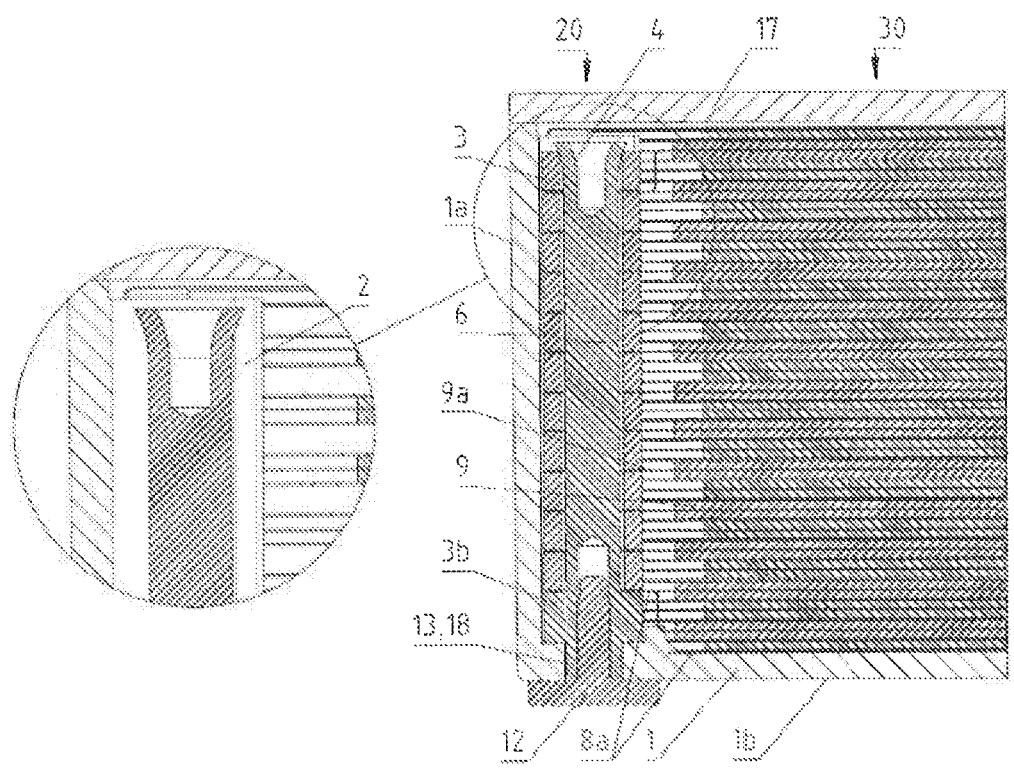
FIG. 2 shows a cross-section of a second exemplary embodiment, with a riveted sleeve.

FIG. 2 shows a cross-section of a second exemplary embodiment of the accumulator according to the invention, in the region of a contacting device 20 for negative electrodes. Any repetition of the description of features of the second exemplary embodiment which features are identical to those of the first exemplary embodiment has been omitted. By way of a distinction from the first exemplary embodiment, in the second exemplary embodiment, the negative straight contact terminals 9a of a plurality of negative electrodes 9 which are coated on both sides are routed to the contacting device 20. In FIG. 2, the external contact 12 constitutes the negative pole of the accumulator. The contacting device 20 is built up as follows: on the flange 3b of the pin 3, the negative angled contact terminal of a negative electrode which is coated on one side is firstly arranged. This is followed by a negative straight contact terminal 9a. This is followed by an alternating arrangement of a contacting element 6 in the form of a sleeve, and a negative straight contact terminal 9a. At the uppermost end of the stack 30, directly below the housing cover 17, a negative electrode which is coated on one side with active material is arranged. The negative angled contact terminal thereof leads to the contacting device 20, and is arranged on a negative straight contact terminal 9a. Above this, a final contacting element 6 is located. In the present second exemplary embodiment, a recess is provided at the second, upper end of the pin 3 for the formation of a riveted connection 4. In the manufacture of an accumulator according to the second exemplary embodiment, the contacting device 20 is compressed together and the riveted connection 4 is then formed. Accordingly, all the negative contact terminals and the contacting elements 6 are clamped between the flange 3b and the riveted connection 4, which functions as a counter-bearing, such that there is the lowest possible contact resistance between the negative contact terminals, the contacting elements and the pin 3.

Figure 3:
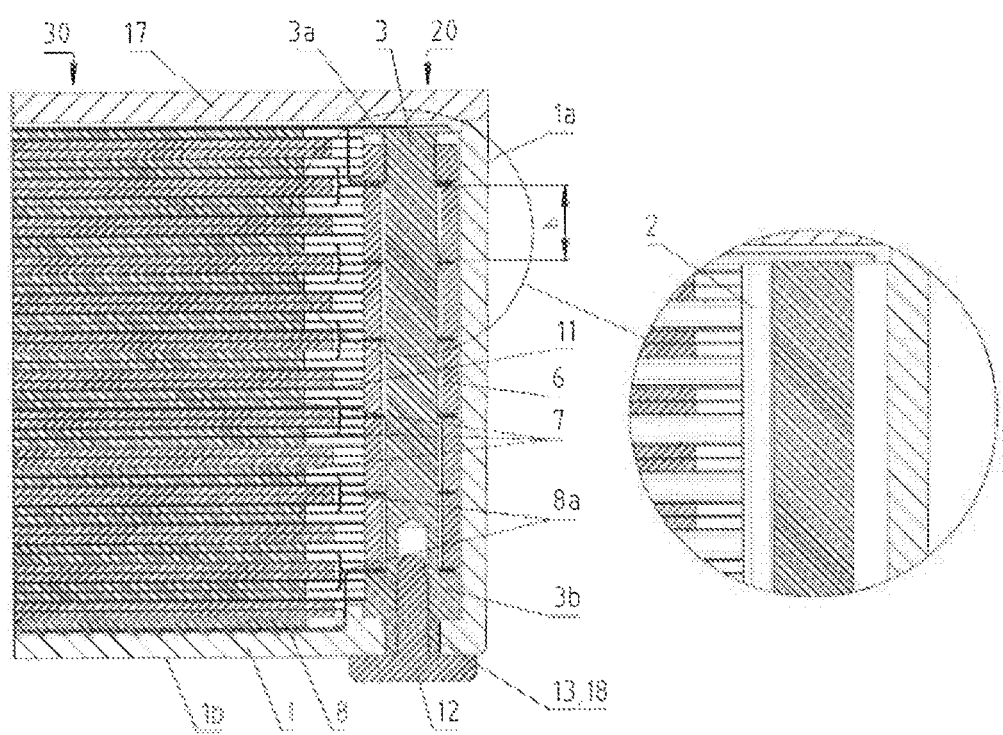
FIG. 3 shows a cross-section of a third exemplary embodiment, with long sleeves and screw fixing.

FIG. 3 shows a cross-section of a third exemplary embodiment of the accumulator according to the invention, in the region of a contacting device 20 for positive electrodes. The third exemplary embodiment is distinguished from the first exemplary embodiment, in that the height h of a contacting element 6 is now doubled, and in that two positive angled contact terminals 8a are arranged respectively between two contacting elements 6. Between the flange 3b and the bottom-most contacting element 6, three positive contact terminals are located, namely in addition to the two positive angled contact terminals 8a of the positive electrodes coated on both sides, also a positive angled contact terminal of the bottom-most one-sided coated positive electrode 8. Correspondingly, by means of the uppermost contacting element 6, of height h, a total of three positive contact terminals are clamped. In the present third exemplary embodiment, the height h of the contacting elements 6 corresponds to the thickness of two positive electrodes which are coated on both sides, plus the thickness of two negative electrodes which are coated on both sides, plus the thickness of four separators 11, and minus the thickness of two positive angled contact terminals 8a. The contacting elements are in turn arranged between two adjoining positive contact terminals, wherein two directly adjoining positive contact terminals respectively have previously been angled and combined, thus forming a new and common positive angled contact terminal.

Figure 4:
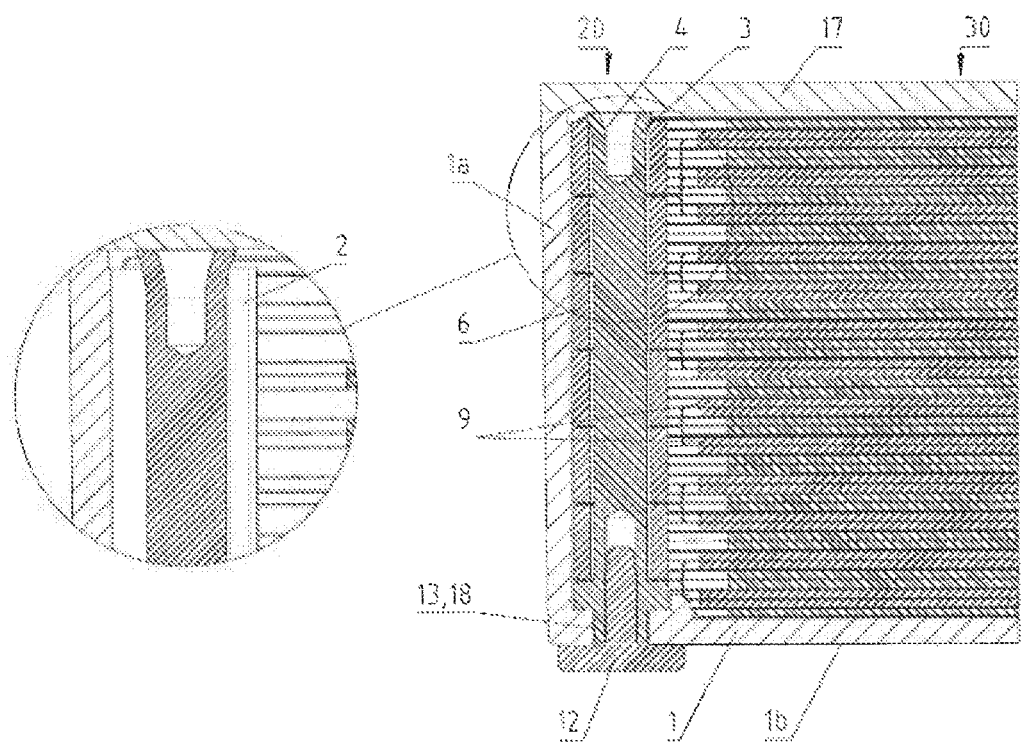
FIG. 4 shows a cross-section of a fourth exemplary embodiment, with long sleeves and riveting.

FIG. 4 shows a cross-section of a fourth exemplary embodiment of the accumulator according to the invention, in the region of a contacting device 20 for negative electrodes. In this case, analogously to the preceding third exemplary embodiment, two respectively directly adjoining negative angled contact terminals are combined, such that the contacting elements assume double the height, in comparison with the first two exemplary embodiments. As a distinction from the third exemplary embodiment, in the fourth exemplary embodiment, the negative electrodes are mutually connected by means of the contacting device 20, and a riveted connection 4 is employed, as in the case of the second exemplary embodiment.

Figure 5:
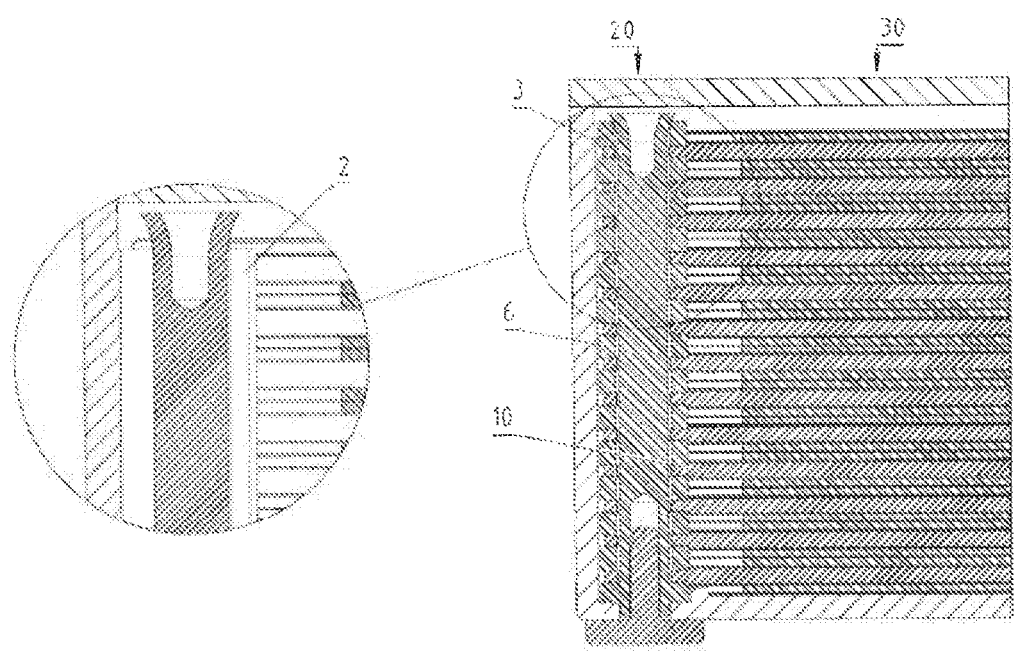
FIG. 5 shows a cross-section of a fifth exemplary embodiment, with graphite electrodes.

FIG. 5 shows a cross-section of a fifth exemplary embodiment of the accumulator according to the invention, in the region of a contacting device 20 for negative electrodes 10 incorporating graphite. The negative electrodes 10, which are coated on both sides, contain no metal, and are provided with a carrier band of graphite, the uncoated part of which functions as a negative straight contact terminal, and is routed directly to the contacting device 20. Consequently, no metallic conductor tabs are required as contact terminals between the active material of the electrode and the contacting device 20. However, the graphite carrier bands can be thicker than metallic conductor tabs, as a result of which the contacting elements 6, in this exemplary embodiment, can have a correspondingly reduced height. Although, in this exemplary embodiment, riveting is employed in the contacting device 20, a screw connection is possible in place of the riveted connection, or a welded connection is also possible.

A common feature of the first to fifth exemplary embodiments is that the pin 3 has the smallest possible diameter in the region of the contacting elements.

Figure 6:
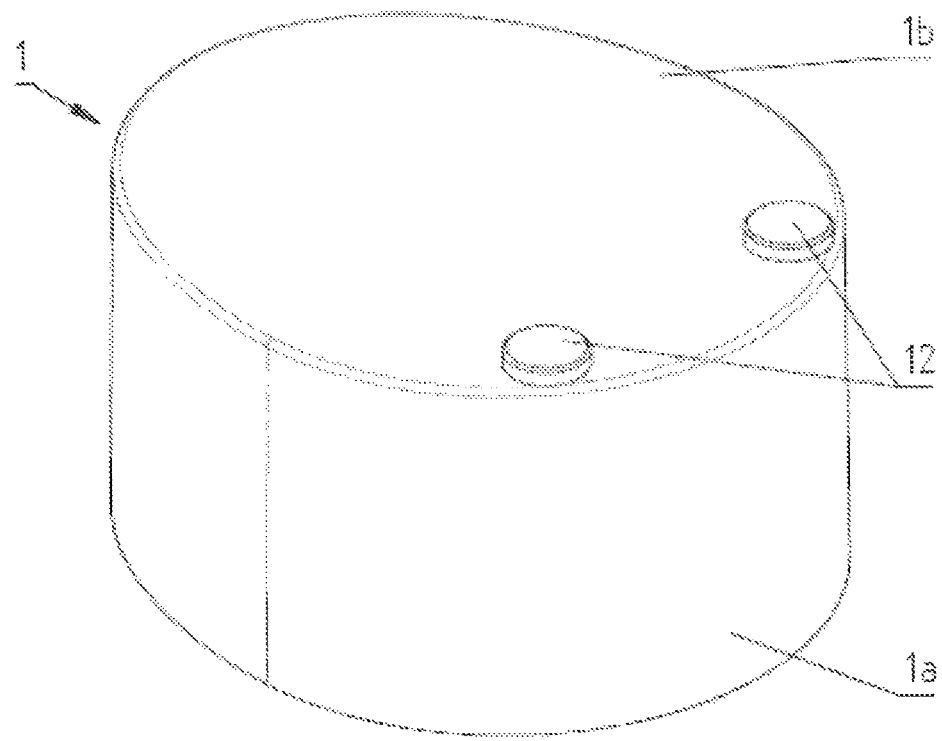
FIG. 6 shows a housing receptacle, viewed laterally from below.

FIG. 6 shows a housing receptacle 1, viewed laterally from below. The two external contacts 12 project from the receptacle base 1b. They constitute the positive pole and the negative pole of the accumulator according to the invention, and are contactable with the (not shown) device which is to be supplied with electrical energy by the accumulator. The external contacts 12 are located in the vicinity of the receptacle wall 1a. The housing receptacle 1 assumes an oval basic shape, and is otherwise cylindrical.

Figure 7:
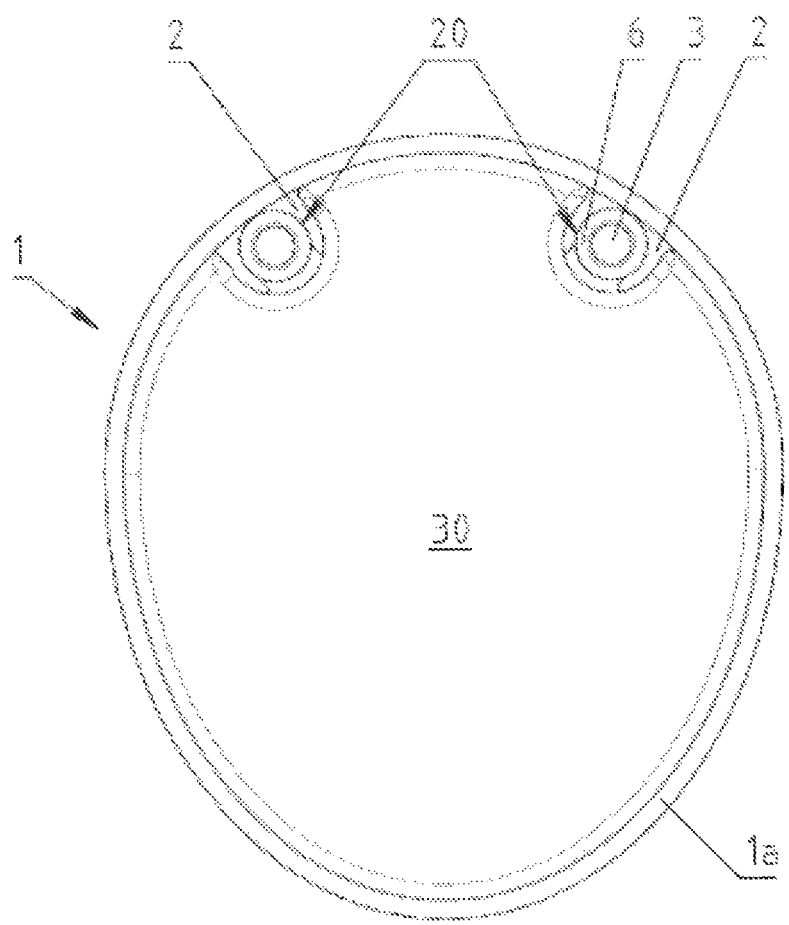
FIG. 7 shows a housing receptacle, viewed from above.

FIG. 7 shows the housing receptacle 1, viewed from above with a removed receptacle base 1b. The stack 30 of positive electrodes and negative electrodes, and separators, is located in the housing receptacle, and occupies almost the entire volume of the housing receptacle. Only the two contacting devices 20 arranged in the immediate vicinity of the receptacle wall 1a, and the claddings 2 thereof, project into the interior space of the housing receptacle, and reduce the volume available for the active material. Each of the two claddings 2 is respectively comprised of a receptacle wall 1a and two projections which are connected to the receptacle wall 1a and project therefrom, such that each contacting device, measured in the circumferential direction, is enclosed by the cladding, to a proportion of approximately 75%. The cladding 2 lies in contact with the contacting device 20. During the assembly of the accumulator according to the invention, the cladding 2 functions as a guide for the contact terminals of the electrodes, which extend through an opening in the cladding 2 into the contacting device 20, and as a guide for the contacting element 6. Additionally, during assembly, the pin 3 can be employed as a guide for the contact terminals and the contacting elements. The housing receptacle 1 is comprised of plastic, and can be formed integrally with the two claddings 2, for example by injection-molding.

Figure 8:
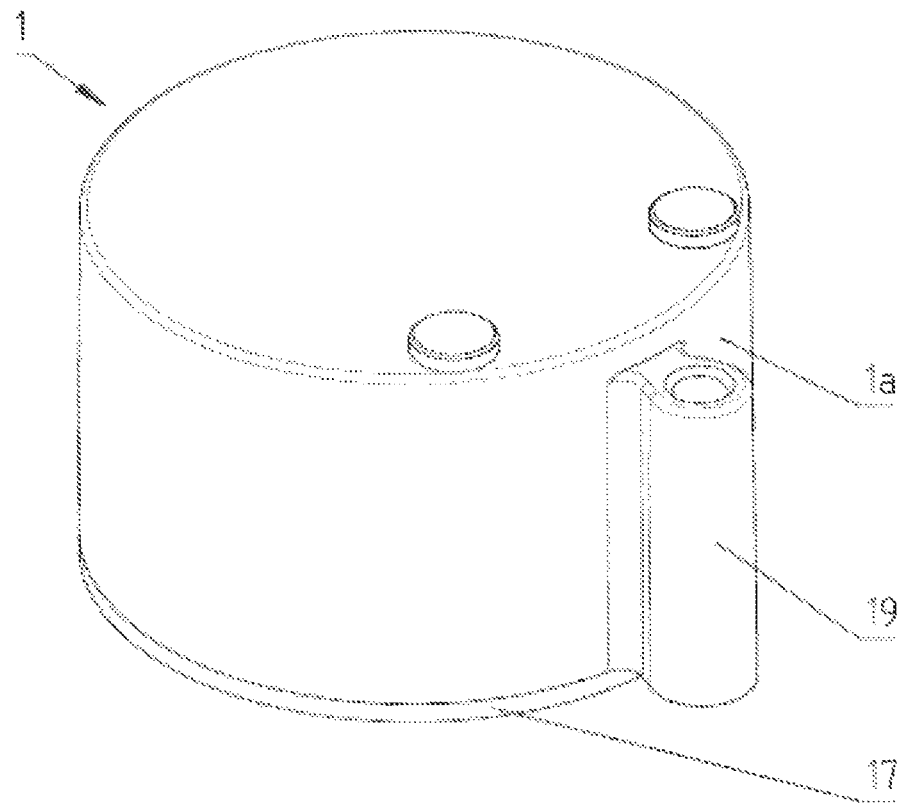
FIG. 8 shows a housing receptacle with an eye, viewed laterally from below.

FIG. 8 shows a housing receptacle 1 with an eye 19, viewed laterally from below. In this exemplary embodiment, the eye 19 is arranged on the receptacle wall 1a, and can be employed for the purposes of fastening in a (not shown) device. The housing receptacle 1 is comprised of plastic, and can be formed integrally with the eye 19, for example by injection-molding. In the interests of completeness, it should further be mentioned that the housing receptacle 1 is closed by a housing cover 17. Accordingly, FIG. 8 represents a finished accumulator according to the invention, viewed from the exterior. In the interior of the housing receptacle 1, an arrangement according to the first, second, third, fourth and/or fifth exemplary embodiment, or a combination thereof, can be located.

Figure 9:
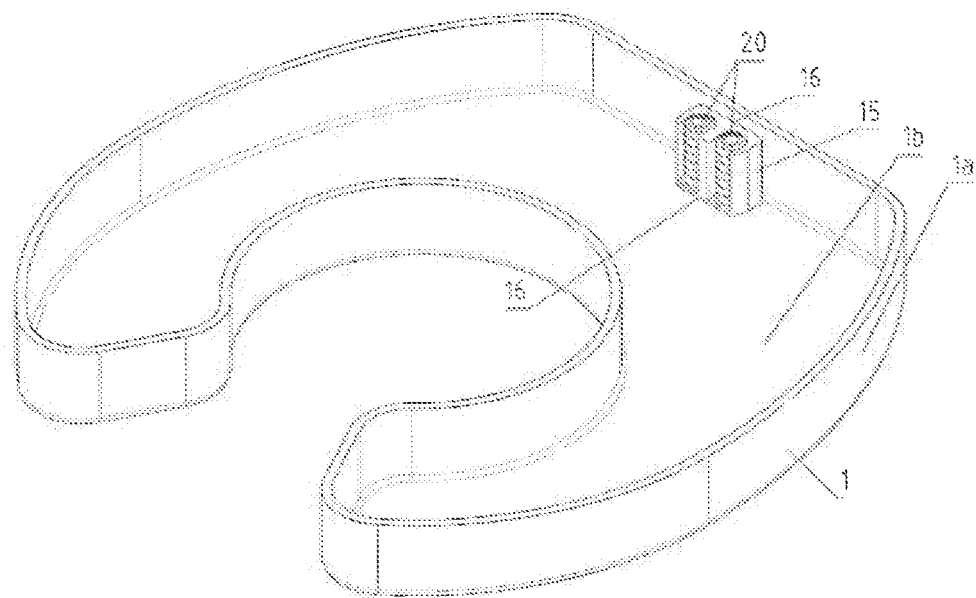
FIG. 9 shows a customized housing receptacle, viewed laterally from above.

FIG. 9 shows an alternative embodiment of a housing receptacle 1 having a customized U-shaped of metal construction, viewed laterally from above. In order to permit the electrical insulation of the contact terminals with respect to the housing receptacle 1, a spectacle-shaped plastic part 15 for the accommodation of two contacting devices 20 is arranged on one edge of the housing receptacle 1. The spectacle-shaped plastic part 15 can specifically be insulated in relation to the housing receptacle 1 by means of an external insulator 16. In the interests of clarity, the stack 30 of electrodes and separators is not shown in FIG. 9.

The variants of the accumulator according to the invention described in the first to fifth exemplary embodiments can be mutually combined in a variety of ways. For example, the first exemplary embodiment and the second exemplary embodiment can be mutually combined to form a further exemplary embodiment such that, within an accumulator according to the invention, both the positive electrodes are connected to a contacting device, and the negative electrodes are connected to a further contacting device. Further variants are provided, wherein both contacting devices, at their upper end, can be screwed (see FIG. 1), riveted (see FIG. 2), or welded. The third exemplary embodiment and the fourth exemplary embodiment can be combined analogously. A combination of the fifth exemplary embodiment (graphite electrodes) with the first exemplary embodiment is particularly advantageous. If the fifth exemplary embodiment (graphite electrodes) is combined with the concept of the fourth exemplary embodiment (doubling of the height of the contacting elements), the resulting outcome can also be effectively combined with the third exemplary embodiment. In this manner, a variety of potential combinations can be produced, not all of which are comprehensively and explicitly listed here, but which can be inferred by a person skilled in the art with no further instruction.

In summary, it can be observed that the present invention, specifically for small accumulators, provides a substantial improvement in energy density and/or capacity, as the space-saving execution of the contacting device, and the cladding thereof, provides more available space for active material than in the case of conventional accumulators.

The invention claimed is:

1. Accumulator for the storage and release of electrical energy, comprising:
    a) at least two positive electrodes, each with a contact terminal,
    b) at least two negative electrodes, each with a contact terminal,
    c) at least one contacting device having at least one contacting element which is arranged between two adjoining contact terminals and interconnects said two adjoining contact terminals in an electrically conductive manner, d) a housing, which entirely accommodates the at least two positive electrodes, the at least two negative electrodes, and the at least one contacting device, e) the accumulator comprises at least one cladding structure, which encloses the at least one contacting device, wherein f) the contacting device comprises a clamping device, which clamps the at least one contacting element to the at least two adjoining contact terminals.

2. The accumulator according to claim 1, wherein a) the at least two adjoining contact terminals each comprise a hole, b) the at least one contacting element is a sleeve, and c) the clamping device comprises a pin and a counter-bearing, wherein the pin, in a region of a first end, has a flange and, in a region of a second end, has a connection to the counter-bearing, and wherein the pin is routed through the holes in the at least two adjoining contact terminals and through the at least one contacting element, and wherein the at least two adjoining contact terminals and the at least one contacting element are arranged between the flange and the counter-bearing.

3. The accumulator according to claim 2, wherein the connection of the pin to the counter-bearing is a threaded connection, a riveted connection and/or a welded connection.

4. The accumulator according to claim 1, wherein the contact terminals of the at least two positive electrodes are adjoining and/or the contact terminals of the at least two negative electrodes are adjoining.

5. The accumulator according claim 1, wherein the accumulator comprises two contacting devices, both of which are entirely arranged within the housing.

6. The accumulator according to claim 1, wherein the cladding is consisting of a plastic.

7. The accumulator according to claim 1, wherein the housing is consisting of a plastic.

8. The accumulator according to claim 1, wherein the housing comprises an eye which is arranged on an outer side of the housing.

9. The accumulator according to claim 1, wherein at least one of the negative electrodes comprises a current conductor of an electrically conducting non-metallic structural material.

10. Method for manufacturing an accumulator according to claim 1, comprising the following steps:

a) the alternating insertion of a positive electrode with a contact terminal and a negative electrode with a contact terminal in a housing, such that the contact terminal of the positive electrode is arranged in a cladding and/or such that the contact terminal of the negative electrode is arranged in a cladding, b) the application of a contacting element to the contact terminal of a positive electrode and/or the application of a contacting element to the contact terminal of a negative electrode, c) repetition of step b), d) production of at least one contacting device by the formation of an electrically conductive connection between the contacting element and two adjoining contact terminals.

11. The method according to claim 10, wherein step d) includes riveting, screwing and/or welding of a counter bearing to a pin.

12. The method according to claim 10, additionally comprising one or more of the following steps:

e) the punch-out and ablation of the positive electrodes and the negative electrodes, according to predefined shapes, and/or f) the at least partial coating of a pin with a seal, and/or g) press-fitting of a pin through a housing bushing in the receptacle base to an external contact, and/or h) welding of the negative electrodes in one separator respectively, and/or i) drying, insertion of electrolyte, gas-tight fitting of the housing cover and formation of the accumulator.

* * * * *